March 12, 1963 C. FISCHER Plant Pat. 2,233
GLADIOLUS PLANT
Filed March 27, 1962
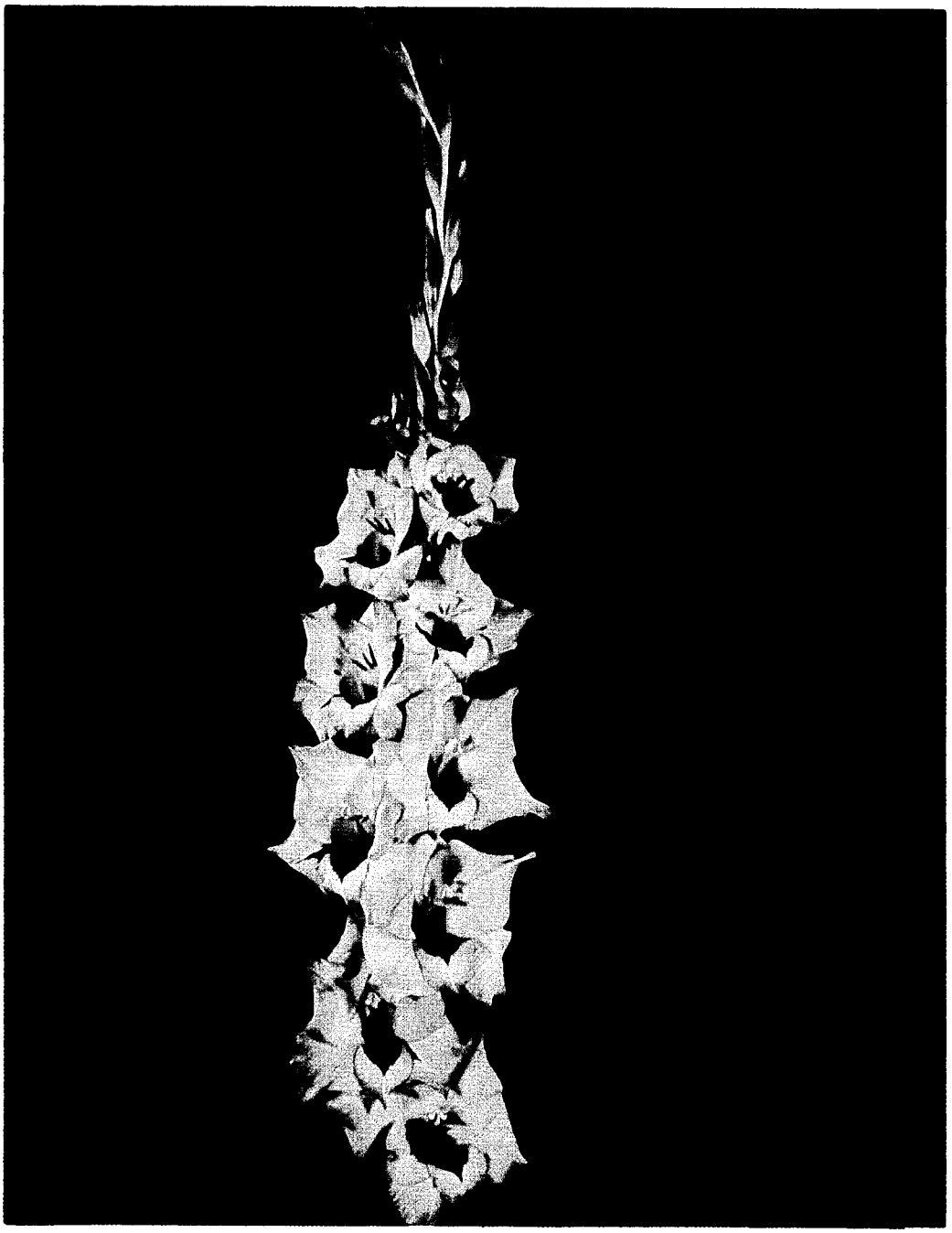
Inventor.
Carl Fischer
By: Robb & Robb
Attorneys.

United States Patent Office

Plant Pat. 2,233
Patented Mar. 12, 1963

2,233
GLADIOLUS PLANT

Carl Fischer, St. Charles, Minn., assignor to Imperial Flowers Limited, Leamington, Ontario, Canada, a corporation of Canada Filed Mar. 27, 1962, Ser. No. 182,986
1 Claim. (Cl. 47—60)

The present invention relates to a new and distinct variety of gladiolus plant which was originated by me by crossing the variety "Admiral" (unpatented) with the variety "Caribbean" (unpatented), the former of which was the seed parent and the latter the pollen parent.

As the result of this breeding, which was performed by manual cross pollination in my outdoor breeding fields at St. Charles, Minnesota, I have produced a new and improved variety of gladiolus plant which is distinguished from its parents, as well as from all other varieties of which I am aware, as evidenced by the following unique combination of characteristics which are outstanding in the new variety:

(1) Exceptional straightness of the flower stem;
(2) A round and smooth bulb form; and
(3) A distinctive and attractive violet general color tonality of the flowers, combined with a distinctive and pleasing blotch effect of purple and white color.

My new variety resembles the variety known as "Novelty Blue" (unpatented) more than any other known variety, but differs therefrom particularly by the smoother bulbs of the new variety, thinner but straighter and more willowy stem which stands much straighter in the field, and a cleaner flower color.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticulture Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely vigorous; average propagator; flower spike attains height of about 54 inches to 58 inches.

Blooming habit: Mid-season; comes into bloom in the northern latitudes of the United States approximately 85 days from the planting of large bulbs.

Stems: Very straight and stiff.
*Diameter at base.*—About ⅜ inch.
*Color (above the bulb).*—Rose-purple.

Foliage: Slender; upright; from about 46 inches to 48 inches tall; leaves range from 1¼ inches to 1½ inches in width. Color—healthy green.

Disease resistance: Unusually resistant to Fusarium yellows, Sclerotina dry rot and Septoria leaf spot, as determined by comparison with other varieties grown in my fields near St. Charles, Minnesota, in irrigated black loam soil.

Corms (bulbs): Normal; plump; healthy; thin husk. Color of flesh—Chrome Yellow, Plate 605/2.

*Flower*

Spike: Tall; bears from 20 to 22 buds of which 7 or 8 are usually open at the same time and with 7 or 8 buds showing color.

Bud:
*Size.*—About 3 inches long when opening.
*Opening.*—7 or 8 buds show color at one time.

Flower:
*Arrangement.*—Florets are semi-formally arranged on stem and usually all facing forward.
*Size.*—Individual florets range from 5¼ inches to 5½ inches in diameter, with upper blooms being progressively smaller.
*Form.*—Triangular shaped florets and somewhat needle-pointed.
*Keeping qualities.*—Average.

Petals:
*Shape.*—Triangular; recurved; needle-pointed.
*Size.*—Outer petals—2½ inches wide. Lip petal—1½ inches wide.
*Aspect.*—Smooth surface; average substance.
*Fragrance.*—None.
*Color.*—Aster Violet, Plate 38/2, with Campanula Violet, Plate 37/2 at the edges and on the reverse of the petals, and with blotch of Dahlia Purple, Plate 931, and creamy white.

*Reproductive Organs*

Stamens: Color—light violet.
Pistil: Color—white.

I claim:

A new and distinct variety of gladiolus plant, substantially as herein shown and described, characterized particularly as to novelty by the unique combination of a distinctive straightness of stem, round and smooth bulb form, and a distinctive and attractive general color tonality of the flowers corresponding to Aster Violet, with Campanula Violet at the edges and on the reverse of the petals of the florets, said petals being blotched with Dahlia Purple and creamy white.

No references cited.